(12) United States Patent
Puglisi et al.

(10) Patent No.: US 7,297,532 B2
(45) Date of Patent: Nov. 20, 2007

(54) SURFACE BASED TRANSLATION SYSTEM

(75) Inventors: Joseph D. Puglisi, Stanford, CA (US); Scott C. Blanchard, Palo Alto, CA (US); Ruben L. Gonzalez, Hayward, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 402 days.

(21) Appl. No.: 10/352,504

(22) Filed: Jan. 27, 2003

(65) Prior Publication Data

US 2003/0219783 A1 Nov. 27, 2003

Related U.S. Application Data

(60) Provisional application No. 60/351,846, filed on Jan. 25, 2002.

(51) Int. Cl.
*C12N 1/00* (2006.01)
(52) U.S. Cl. .................................................. 435/317.1
(58) Field of Classification Search .............. 435/317.1
See application file for complete search history.

(56) References Cited

U.S. PATENT DOCUMENTS

| 5,478,730 | A | 12/1995 | Alakhov et al. |
| 6,660,473 | B1 | 12/2003 | Lohse |
| 7,125,669 | B2 * | 10/2006 | Kurz ............................. 435/6 |

OTHER PUBLICATIONS

Sytnik A. et al. "Peptidyl transferase center activity observed in single ribosomes", J. Mol. Biol., 1999, 285: 49-54. entire document.*
Poot R.A. et al. Separation of mutant and wild-type ribosomes based on differences in their anti Shine-Dalgamo sequence, Nucleic Acids Research, 1993, vol. 21, No. 23, pp. 5398-5402, entire document.*
Amstutz et al., In Vitro Display Technologies: Novel Developments and Applications, Curr Opin Biotechnol, (2001), 200112(4): 400-5.
Green and Puglisi, The Ribosome Revealed, Nat Struct Biol, (1999), 6(11): 999-1003.
Ha et al., Ligand-Induced Conformational Changes Observed in Single RNA Molecules, Proc Natl Acad Sci, (1999), U S A 96(16): 9077-82.
Ha et al., Single-Molecule Fluorescence Spectroscopy of Enzyme Conformational Dynamics and Cleavage Mechanism, Proc Natl Acad Sci, (1999), U S A 96(3): 893-8.
Hanes et al., Selecting and Evolving Functional Proteins In Vitro by Ribosome Display, Methods Enzymol, (2000), 328: 404-30.
Lafontaine et al., The Function and Synthesis of Ribosomes, Nat Rev Mol Cell Biol, (2001), 2(7): 514-20.
Puglisi et al., Approaching Translation at Atomic Resolution, Nat Struct Biol, (2000), 7(10): 855-61.
Weiss, Science, Fluorescence Spectroscopy of Single Biomolecules, (1999), 283(5408): 1676-83.
Zhuang et al., A Single-Molecule Study of RNA Catalysis and Folding, Science, (2000), 288(5473): 2048-51.
Kurz et al., Psoralen photo-crosslinked mRNA-puromycin conjugates: a novel template for the rapid and facile preparation of mRNA-protein fusions, Nucleic Acids Research, 2000, 28(18): e83i-e83v.
Okamoto et al., Synthesis and Properties of Peptide Nucleic Acids Containing a Psoralen Unit, Org. Lett., 2001, 3(6): 925-927.

* cited by examiner

*Primary Examiner*—Sandra E. Saucier
*Assistant Examiner*—Satyendra K. Singh
(74) *Attorney, Agent, or Firm*—Bozicevic Field & Francis LLP; Pamela J. Sherwood

(57) ABSTRACT

Translationally competent ribosomes are bound to a solid substrate through a specific attachment site. A spatial array of such immobilized ribosomes may be produced on a planar substrate, microbeads, on fiber optics. One or more components of the ribosome complex are preferably labeled, e.g. with a fluorescent dye. Ribosomal RNAs, including mRNA and tRNA; and/or ribosomal proteins may be labeled at specific positions, and arrays of immobilized ribosomes may comprise a panel of different labels and positions of labels. Fluorescence detection can then be used to monitor conformational dynamics and translation rates.

15 Claims, No Drawings

SURFACE BASED TRANSLATION SYSTEM

STATEMENT REGARDING GOVERNMENT RIGHTS

This invention was supported at least in part by grant number GM51266 from the National Institutes of Health. The U.S. Government may have certain rights in the invention.

BACKGROUND OF THE INVENTION

Protein synthesis is performed by the ribosome, which in conjunction with many exogenous factors converts the genetic code into protein. Translation has important practical aspects. The ribosome is a target for many clinically important antibiotics, and tools to monitor the ribosome and translation find use in drug screening. Translation also provides the route from gene to expressed protein. Although laboratory based protein synthesis can be performed, it is a cumbersome process, and improved methods of synthesis, for example to produce peptide drugs, are of interest.

Pharmaceutical drug discovery, a multi-billion dollar industry, involves the identification and validation of therapeutic targets, as well as the identification and optimization of lead compounds. The explosion in numbers of potential new targets and chemical entities resulting from genomics and combinatorial chemistry approaches over the past few years has placed enormous pressure on screening programs. There is a need in drug development to determine the ability of a test compound to affect a potential drug target. It is therefore of great interest to provide a rapid, efficient and inexpensive quantification and screening technique.

The ribosome is the central component of the cellular protein synthesis machinery, which catalyzes peptide bond formation between amino acids attached to transfer RNAs (tRNAs) on adjacent codons of a mRNA. Like all enzymes involved in genetic information transfer, the ribosome must perform protein synthesis in a processive manner at a rapid rate, while maintaining the fidelity of information transfer. As a central process in information transfer, the ribosome and translation is often regulated by external factors and element of the mRNA.

A large body of genetic and biochemical data has established the basic aspects of translation. The 30S subunit interacts with the anticodon portion of the tRNA ligands, whereas the 50S subunit interacts with the 3' ends of the tRNAs. Ribosomal RNA plays a central role in ribosome function. Conserved portions of ribosomal RNA form the binding sites for the tRNA ligands in the peptidyl tRNA (P site) aminoacyl-tRNA (A site) and the exit site for deacylated tRNA (E site). The peptidyl transferase active site consists solely of RNA. Ribosomal proteins also play a critical role in ribosome function; mutations in ribosomal proteins S12 and S5 cause drug resistance and fidelity phenotypes whereas L7/L12 is critical for factor binding. Protein and RNA work in concert to form the active particle.

The ribosome is the target of a many antibiotics. These small compounds, which include aminoglycosides, tetracyclines, macrolides and chloramphenicols, interfere with distinct steps in translation, including initiation, elongation and termination. Many of the ribosome-directed antibiotics target rRNA, which form the critical functional sites on the ribosome. The antibiotics are thus both powerful mechanistic tools to dissect individual steps of protein synthesis, and lead compounds for the development of novel therapeutic agents. The ribosome and translation are important targets for therapeutic intervention, not only for treatment of infectious disease, but also treatment of human diseases that involve protein expression.

The rich structural information on the ribosome lies in stark contrast to knowledge of its dynamics. Systems that would permit the analysis of translation are of great interest for synthetic and screening methods.

Relevant Publications

The analysis of single molecule fluorescence is disclosed in, for example, Ha et al. (1999) Proc Natl Acad Sci U S A 96(3): 893-8; Ha et al. (1999) Proc Natl Acad Sci U S A 96(16): 9077-82; Weiss (1999) Science 283(5408): 1676-83; and Zhuang et al. (2000) Science 288(5473): 2048-51.

The use of ribosome display is discussed, for example, by Amstutz et al. (2001) Curr Opin Biotechnol 200112(4):400-5; and by Hanes et al. (2000) Methods Enzymol 2000;328: 404-30.

Ribosome structure and function are reviewed by Puglisi et al. (2000) Nat Struct Biol 7(10):855-61; and Green and Puglisi (1999) Nat Struct Biol 6(11):999-1003. Eukaryotic ribosome function is reviewed, for example, by Lafontaine et al. (2001) Nat Rev Mol Cell Biol 2(7):514-20.

SUMMARY OF THE INVENTION

Compositions and methods are provided for surface based translation, where translationally competent ribosome complexes are immobilized on a solid surface. The ribosomes may be labeled to permit analysis of single molecules for determination of ribosomal conformational changes and translation kinetics. One or more components of the ribosome complex may be labeled at specific positions, and arrays of ribosome complexes may comprise a panel of different labels and positions of labels. The solid phase protein synthesis provided by the surface bound ribosome complex allows translation of a large number of mRNAs to be performed simultaneously in a spatially directed fashion on a surface.

The surface bound system of the present invention allows the detection of an effect on translation from altering the translational environment, where the environment may include exogenous agents, e.g. drug candidates; mRNA sequence changes; salt concentration; pH, the presence of factors; and the like. Such methods are useful in qualitative, quantitative, and competitive assays, e.g. in screening antibiotics, optimization of mRNA sequence for translation, optimization of in vitro translation conditions, etc. The surface bound translation system also finds use in the large scale translation of proteins. The surface bound translation system is applicable to prokaryotic, archael, eukaryotic cytoplasmic and mitochondrial ribosomes

DETAILED DESCRIPTION OF THE INVENTION

Compositions and methods are provided for immobilizing translationally competent ribosome complexes on a solid surface. The site of attachment is selected so as to avoid steric interference with translation, and may be accomplished through the use of a specific binding partner to ribosomal RNAs; mRNA; ribosomal proteins, and other polynucleotide or polypeptide components. A spatial array of immobilized ribosomes may be produced on a planar substrate, microbeads, on fiber optics; and the like.

The ribosomes may be labeled, e.g. with a fluorescent dye. Ribosomal RNAs, including mRNA and tRNA; ribosomal proteins; and other factors and agents involved in translation may be labeled at specific positions, and arrays of immobilized ribosomes may comprise a panel of different labels and positions of labels.

Detection of the label can then be used to monitor conformational dynamics, such as the elongation rate of protein synthesis. Single molecule analysis can detect rare conformational events that are not observed in bulk, ensemble-averaged measurements, and allow heterogeneity in the system to be sorted and characterized. For multistep processes such as translation, single molecule analysis eliminates the requirement for synchronization of large numbers of molecules. Distance scales probed by methods such as fluorescence resonance energy transfer (FRET) are on the order of about 20-80 Å, which permits determination of ribosomal conformational changes and translation kinetics. To perform single-molecule analysis of a biomolecular system, the molecules are specifically localized on a derivatized quartz surface, where the attachment to the surface allows spatial localization of the particle to the optical limit of the microscope without impairing its function.

The surface bound system of the present invention allows the detection of an effect on translation from altering the translational environment, where the environment may include exogenous agents, e.g. drug candidates; mRNA sequence changes; salt concentration; pH, the presence of factors; and the like. Such methods are useful in qualitative, quantitative, and competitive assays, e.g. in screening antibiotics, optimization of mRNA sequence for translation, optimization of in vitro translation conditions, etc. The surface bound translation system also finds use in the large scale translation of proteins.

In some embodiments of the invention, the polypeptide product is screened for function, presence of epitopes, binding, etc., by localizing the polypeptide product at or near the site of the surface bound ribosome, for example by independently binding the polypeptide to the surface, by maintaining the polypeptide bound to the ribosome, and the like.

Definitions

Before the present methods are described, it is to be understood that this invention is not limited to particular methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a specific binding pair" includes a plurality of such specific binding pairs and reference to "the complementing domain" includes reference to one or more complementing domains and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Translationally competent ribosome. Ribosomes are ribonucleoprotein particles that performs protein synthesis using a messenger RNA template. The ribosome, a 70S particle in prokaryotes, is composed of two sub-units. The small sub-unit (30S) mediates proper pairing between transfer RNA (tRNA) adaptors and the messenger RNA, whereas the large subunit (50S) orients the 3 ends of the aminoacyl (A-site) and peptidyl (P-site) tRNAs and catalyzes peptide bond formation. The ribosome translocates directionally along mRNA in 3 nucleotide steps to read the sequential codons. For the purposes of the present invention, ribosomes may be prokaryotic or eukaryotic. The term "ribosome complex" may be used herein to refer to a complex of ribosome in association with one or more biomolecules associated with translation, including, without limitation, mRNA, tRNAs, nascent polypeptide, elongation and initiation factors.

As used herein, translational competence is the ability of a ribosome to catalyze at least one peptide bond formation where the tRNA and mRNA template are properly paired, and may include the ability to catalyze translation of a complete mRNA into the appropriate protein.

It will be understood by those of skill in the art that other components may be required for translation, including, for example, amino acids, nucleotide triphosphates, tRNAs and aminoacyl synthetases, or aminoacyl-loaded tRNAs; elongation factors and initiation factors. In addition the reaction mixture may comprise enzymes involved in regenerating ATP and GTP, salts, polymeric compounds, inhibitors for protein or nucleic acid degrading enzymes, inhibitor or regulator of protein synthesis, oxidation/reduction adjuster, non-denaturing surfactant, buffer component, spermine, spermidine, etc. The salts preferably include potassium, magnesium, ammonium and manganese salt of acetic acid or sulfuric acid, and some of these may have amino acids as a counter anion. The polymeric compounds may be polyethylene glycol, dextran, diethyl aminoethyl, quaternary aminoethyl and aminoethyl. The oxidation/reduction adjuster may be dithiothreitol, ascorbic acid, glutathione and/or their oxides. Also, a non-denaturing surfactant, e.g. Triton X-100 may be used at a concentration of 0-0.5 M. Spermine and spermidine may be used for improving protein synthetic ability. Preferably, the reaction is maintained in the range of pH 5-10 and a temperature of 20°-50° C., and more preferably, in the range of pH 6-9 and a temperature of 25°-40° C.

In some embodiments of the invention, the ribosome comprises rRNA that has been genetically modified, e.g. to introduce attachment sites, sites for labeling, etc. The genetic modification can be introduced into the chromosome of the host cell from which the ribosome is derived, or more conveniently is introduced on an episomal vector, e.g. phage, plasmid, phagemid, and the like. Preferably the host cell into which the vector is introduced will lack the corresponding native rRNA genes. Ribosomes are therefor assembled using cellular machinery. The ribosomes are purified from the host cell by conventional methods known to those of skill in the art.

Substrate attachment Translationally competent ribosomes or ribosome complexes are attached to a solid surface at a specific attachment site, where the attachment site is one of a specific binding pair. Preferably the attachment site is other than the nascent polypeptide component that is being translated. The attachment site may be naturally occurring, or may be introduced through genetic engineering. Preformed ribosome complexes can be attached to the surface, or complexes can be assembled in situ on the substrate. The ribosome or ribosome complex is usually stably bound to the substrate surface for at least about 1 minute, and may be stably bound for at least about 30 minutes, 1 hour, or longer, where the dissociation rate of the complexes depends on solution conditions and ligand-bound state of the ribosome. Complexes are usually more stable at higher $Mg^{++}$ concentrations and monovalent ion concentrations. The complex stability may also be increased at lower pH, by the presence of a P-site tRNA, and by addition of an acyl-aminoacid on the tRNA.

In one embodiment of the invention, the attachment site is a nucleic acid sequence present in one of the ribosomal RNAs or on the mRNA, where a polynucleotide having a sequence complementary to the attachment site acts a linker between the ribosome complex and the solid surface. A convenient nucleic acid attachment site is mRNA, usually at the 5' or 3'-end, where a complementary polynucleotide may hybridize, for example, to the untranslated region of the mRNA.

Alternative nucleic acid attachment sites include rRNA regions of conserved A-form helical secondary structure where the primary sequence of the helical region is not evolutionarily conserved. Examples include surface-accessible hairpin loops, particularly those regions that are not involved in tertiary structure formation. Such regions may be identified by a comparison of rRNA sequences to determine a lack of sequence similarity. Criteria include a helix of at least about 5 nt. in length, with a non-conserved nucleotide sequence.

The surface accessible loop may serve as an attachment site, or more preferably, the rRNA will be genetically modified to expand stem loop sequences by from about 6 to about 20 nucleotides, more usually from about 8 to about 18 nucleotides. Preferred rRNA suitable for such modification is the prokaryotic 16S rRNA or the corresponding eukaryotic 18S rRNA, although the 23S and 28S rRNA may also find use.

Specific sites of interest for the introduction of a stem loop expansion for an attachment site include, without limitation, the 16S rRNA H6, H10, H26, H33a, H39 and H44 loops (Wimberly et al. (2000) Nature 407(6802):327-39). In 23S rRNA, the H9, H68 and H101 may be selected (Ban et al. (2000) Science 289(5481): 905-20).

The polynucleotide having a sequence complementary to the attachment site may be indirectly coupled to the substrate through an affinity reagent comprising two binding partners. Examples of suitable affinity reagents include biotin/avidin or streptavidin; antibody/hapten; receptor/ligand pairs, as well as chemical affinity systems. For example, the substrate surface may be derivatized with avidin or streptavidin, and a ribosome complex comprising a biotin moiety present on a complementary polynucleotide is then contacted with the substrate surface, where specific attachment then occurs.

Where the polynucleotide having a sequence complementary to the attachment site is directly coupled to the substrate, various chemistries may be employed to provide a covalent bond, including homo- or heterobifunctional linkers having a group at one end capable of forming a stable linkage to the polynucleotide, and a group at the opposite end capable of forming a stable linkage to the substrate. Illustrative entities include: azidobenzoyl hydrazide, N-[4-(p-azidosalicylamino)butyl]-3'-[2'-pyridyidithio]propionamide), bis-sulfosuccinimidyl suberate, dimethyladipimidate, disuccinimidyltartrate, N-γ-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl]aminobenzoate, glutaraldehyde, NHS-PEG-MAL; succinimidyl 4-[Nmaleimidomethyl]cyclohexane-1-carboxylate; 3-(2-pyridyidithio)propionic acid N-hydroxysuccinimide ester (SPDP) or 4-(N-maleimidomethyl)-cyclohexane-1-carboxylic acid N-hydroxysuccinimide ester (SMCC). To improve the stability, the substrate may be functionalized to facilitate attachment. Modes of surface functionalization include silanization of glass-like surfaces by 3-aminopropyltriethoxysilane, 3-mercaptopropyltrimethoxysilane, 3-isocyanatopropyltriethoxysilane, 3-isothiocyanonatopropyltriethoxysilane, 2-(4-chlorosulfonylphenyl)ethyltrimethoxysilane, 3-bromopropyltrimethoxysilane, methacryloxymethyltrimethylsilane; and the like. Polymer coating may be achieved with polyvinyl alcohol, polyethyleneimine, polyacrolein, polyacrylic acid, etc.

An alternative attachment strategy utilizes ribosomal proteins, which may be modified to include a site for biotinylation, or other binding moieties.

By "solid substrate" or "solid support" is meant any surface to which the ribosome or ribosome complexes of the subject invention are attached. Where the ribosome is to be fluorescently labeled, a preferred substrate is quartz. Other solid supports include glass, fused silica, acrylamide; plastics, e.g. polytetrafluoroethylene, polypropylene, polystyrene, polycarbonate, and blends thereof, and the like; metals, e.g. gold, platinum, silver, and the like; etc. The substrates can take a variety of configurations, including planar surfaces, beads, particles, dipsticks, sheets, rods, etc.

In one embodiment of the invention, the substrate comprises a planar surface, and ribosomes or ribosome complexes are attached to the surface, e.g. in a solid or uniform pattern, or in an array in a plurality of spots. The density of attached particles on the substrate will be such that a signal from a label can be detected. Where the complexes are spotted on the array, the spots can be arranged in any convenient pattern across or over the surface of the support, such as in rows and columns so as to form a grid, in a circular pattern, and the like, where generally the pattern of spots will be present in the form of a grid across the surface of the solid support. The total number of spots on the substrate will vary depending on the sample to be analyzed, as well as the number of control spots, calibrating spots and the like, as may be desired.

In another embodiment, the substrate is a collection of physically discrete solid substrates, e.g. a collection of beads, individual strands of fiber optic cable, and the like. Each discrete substrate can have complexes distributed across the surface or attached in one or more probe spots on the substrate. The collection of physically separable discrete substrates may be arranged in a predetermined pattern or may be separated in a series of physically discrete containers (e.g., wells of a multi-well plate).

Labeling strategies. In a preferred embodiment of the invention, one or more components of the ribosome complex comprise a fluorescent label. Suitable components include tRNAs, ribosomal proteins, elongation factors, mRNA, ribosomal RNAs, and analogs thereof, such as antibiotics that specifically bind the complex. The label may provide single molecule fluorescence, where the signal from a single fluorochrome is detected; or energy transfer, e.g. fluorescence resonance energy transfer (FRET), where a pair of fluorescent molecules interact to provide a signal. Similar experiments can be performed on large numbers of ribosomes in bulk solution.

Fluorescent labels of interest include: fluorescein, rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N, N, N', N'-tetramethyl-6-carboxyrhodamine (TAMRA), the cyanine dyes, such as Cy3, Cy5, Alexa 542, Bodipy 630/650, fluorescent particles, fluorescent semiconductor nanocrystals, and the like.

FRET occurs when a suitable fluorescent energy donor and an energy acceptor molecule are in close proximity to one another. The excitation energy absorbed by the donor is transferred non-radiatively to the acceptor which can then further dissipate this energy either by fluorescent emission if a fluorophore, or by non-fluorescent means if a quencher. A donor-acceptor pair comprises two fluorophores having overlapping spectra, where the donor emission overlaps the acceptor absorption, so that there is energy transfer from the excited fluorophore to the other member of the pair. It is not essential that the excited fluorophore actually fluoresce, it being sufficient that the excited fluorophore be able to efficiently absorb the excitation energy and efficiently transfer it to the emitting fluorophore.

The donor fluorophore is excited efficiently by a single light source of narrow bandwidth, particularly a laser source. The emitting or accepting fluorophors will be selected to be able to receive the energy from the donor fluorophore and emit light. Usually the donor fluorophores will absorb in the range of about 350-800 nm, more usually in the range of about 350-600 nm or 500-750 nm, while the acceptor fluorophores will emit light in the range of about 450-1000 nm, usually in the range of about 450-800 nm. The transfer of the optical excitation from the donor to the acceptor depends on the distance between the two fluorophores. Thus, the distance must be chosen to provide efficient energy transfer from the donor to the acceptor.

The fluorophores for FRET pairs may be selected so as to be from a similar chemical family or a different one, such as cyanine dyes, xanthenes or the like. Reporter, or donor, dyes of interest include: fluorescein dyes (e.g., 5-carboxyfluorescein (5-FAM), 6-carboxyfluorescein (6-FAM), 2',4',1,4,-tetrachlorofluorescein (TET), 2',4', 5',7',1,4-hexachlorofluorescein (HEX), and 2',7'-dimethoxy-4',5'-dichloro-6-carboxyfluorescein (JOE)), cyanine dyes such as Cy5, dansyl derivatives, and the like. Acceptor dyes of interest include: rhodamine dyes (e.g., tetramethyl-6-carboxyrhodamine (TAMRA), and tetrapropano-6-carboxyrhodamine (ROX)), DABSYL, DABCYL, cyanine, such as Cy3, anthraquinone, nitrothiazole, and nitroimidazole compounds, and the like.

Specific sites of interest for labeling include tRNA, which may be labeled on the RNA or the amino acid portion of the molecule. Body labeling of the RNA itself can be accomplished, for example by synthesizing the tRNA with an amino linker, which can be derivatized. Suitable sites include the anticodon stem loop, the elbow region and 3'acceptor arm. Alternatively, the amino acids used to charge the tRNA can be labeled and then used to charge the tRNA with the appropriate aminoacyl synthetase.

Many proteins involved in the process of translation can be labeled, including ribosomal proteins, elongation and initiation factors, and the like. For example, the S21 protein sits in the tRNA exit site of the ribosome (E site), and can be dye labeled by any conventional method. The labeled protein is separated from the unbound dye, and then incubated with the suitable ribosomal subunit at a molar excess of protein to favor exchange of the native protein with the labeled protein.

Direct fluorescent labeling of ribosomal RNA can utilize a complementary polynucleotide probe that is complementary to a target sequence, where a labeled polynucleotide specifically hybridizes to a rRNA sequence. Target sites on the rRNA for hybridization include regions of conserved A-form helical secondary structure where the primary sequence of the helical region is not evolutionarily conserved. Examples include surface-accessible hairpin loops, particularly those regions that are not involved in tertiary structure formation. Such regions may be identified by a comparison of rRNA sequences to determine a lack of sequence similarity. Criteria include a helix of at least about 5 nt. in length, with a non-conserved nucleotide sequence.

The native sequence may serve as a target site, or more preferably, the rRNA will be genetically modified to expand stem loop sequences by from about 6 to about 20 nucleotides, more usually from about 8 to about 18 nucleotides. Preferred rRNA suitable for such modification is the prokaryotic 16S rRNA or the corresponding eukaryotic 18S rRNA, although the 23S and 28S rRNA may also find use. Specific sites of interest for the introduction of a stem loop expansion for an attachment site include, without limitation, the 16S rRNA H6, H10, H16, H17, H26, H33a, H33b, H39 and H44 loops. In 23S rRNA, the H9, H38, H68 H69, H72, H84, H89, H91 and H101 may be selected.

Alternatively ribosomes may be labeled using a peptide tagging strategy. The BIV Tat protein binds to a specific sequence in the context of an A-form helix with a single-nucleotide bulge; the peptide binds with high affinity (Kd nM) and specificity within the major groove of the helix. See, for example, Campisi et al. (2001) EMBO J 20(1-2): 178-86. Target sites, as described above for hybridization labels, can be genetically modified to contain a BIV Tat binding site, to which is bound fluorescently labeled BIV Tat. The recognition sequence for BIV Tat is 5' NUGNGC 3'; 5' GCNCN 3', where the two strands pair to form a quasi A form paired helix with a single bulged uridine; and where the N-N pair must be a Watson-Crick pair for stability. The BIV Tat peptide generally comprises the amino acid sequence RGTRGKGRRI for high binding affinity. An alternate peptide tag is the HIV Rev peptide, which binds to a purine-rich internal loop in an RNA helix. For double labeling of different subunits, the individual subunits can separated and labeled independently, using combinations of one or more peptide and/or hybridization tags.

Labeled peptide or polynucleotide probes can be synthesized and derivatized with a fluorescent tag. The labeled probes can then be incorporated into cell growth media, or bound to the ribosomes post-synthetically. When bound to the ribosome during synthesis the probes further provide a means investigating the in vivo process of ribosome assembly.

Another approach for rRNA labeling utilizes internal incorporation of dyes by ligation of 16S rRNA fragments that contain dyes at their 5' or 3' termini. For example, 16S rRNA can be transcribed as two pieces, with a dye-labeled dinucleotide as primer of transcription. The two strands are then ligated by DNA ligase and a DNA splint. The 30S subunit is then reconstituted from total 30S proteins using standard protocols.

In another embodiment, the mRNA is labeled. For example, a labeled oligonucleotide may be hybridized downstream on the mRNA of choice, and the hybridized mRNA then combined with a surface bound ribosome complex, where the ribosome complex comprises a label that is a complementary donor/acceptor to the oligonucleotide label. Translation elongation can measured by the interaction of the mRNA with a labeled ribosome. The dye label on the ribosome can be attached to the 30S subunit, near where the 3' end of the mRNA exits from the ribosome, e.g. the cleft near ribosomal protein S5 is the leading edge of the translating ribosome. An alternate labeling approach utilizes reconstituted 30S particles with labeled S5 protein; a number of single-cysteine mutants of S5 have been derivatized and successfully incorporated into 30S subunits.

In another embodiment, labeled DNA oligonucleotides of from about 6 to about 20, usually about 8 to 10 nucleotides are pre-hybridized to mRNA in the test sample, where the site for hybridization is downstream from the initiation codon. Similarly, two labeled oligonucleotides that each comprise one member of a donor acceptor fluorochrome pair may be hybridized successively downstream of the start codon. Alternatively, a labeled oligonucleotide is designed to be complementary to the region of mRNA occluded by the ribosome in the initiation complex.

An alternative method utilizes mRNA that comprises an epitope for which a high affinity antibody is available. Numerous such epitopes are known in the art, e.g. the sequence encoding the amino acid EQKLISEEDL, which is the epitope for high-affinity binding by anti-myc antibody. The epitope will be exposed to the antibody upon its emersion from the 50S subunit exit tunnel, which protects about 40-50 amino acids. Binding of labeled antibody will lead to localization of the label, which means at least about 40-50 amino acids have been synthesized. The epitope tag can be incorporated into any coding sequence of interest, and may be positioned at varying sites throughout the coding sequence. From the time lag before localization of fluorescence as a function of tag position, translation rates can be estimated. As an alternative to an epitope tag, peptide sequences that form fluorescent arsenate complexes can be inserted into the coding sequence. Translation of such modified mRNA is performed in the presence of the labeling arsenic compound.

Detection. Methods of fluorescence detection are known in the art. The detection element may include photodiodes, phototransistors, photomultipliers, and charge-coupled device (CCD) cameras, but is not limited thereto. The signal is then transmitted to a suitable data processor. For single molecule experiments, the internal reflectance (TIR) microscope allows simultaneous detection of hundreds of single molecules, with a time resolution of 100 ms. The fluorescent samples are excited by the evanescent wave generated by total internal reflection of dual laser excitation. Fluorescence is detected using a CCD camera, after the radiation has passed through a dichroic filter.

In the scanning confocal microscope, fluorescence is dual excited and detected using avalance photodiodes. In this instrument, the fluorescence of a single molecule, as opposed to a field of molecules, as in the TIR microscope, is monitored with a time resolution of 1 ms.

Methods and Compositions

In one embodiment of the invention, an array of surface bound ribosome complexes are provided. The array may comprise a single type of ribosome, to which can be added various exogenous agents. Alternatively the array may comprise a panel of ribosome complexes, where there is variation on the site of labels, the type of labels, the mRNA template, and the like. For example, different positions for the label allow detection of specific changes in ribosome conformation and protein synthesis. As described above, the array may be spotted on a planar surface, or present on discrete substrates, such as fibers, microspheres, etc.

In an alternative embodiment, a uniform array of surface bound ribosome complexes may be provided, where bulk protein synthesis can take place. For such purposes, the ribosome complexes need not be labeled.

The surface bound system of the present invention allows the detection of an effect on translation from altering the translational environment, where the environment may include exogenous agents, e.g. drug candidates; mRNA sequence changes; salt concentration; pH, the presence of factors; and the like. Such methods are useful in qualitative, quantitative, and competitive assays, e.g. in screening antibiotics, optimization of mRNA sequence for translation, optimization of in vitro translation conditions, etc. For example, see co-pending patent application 60/351,919, filed concurrently with the present application, and herewith incorporated by reference in its entirety. Some examples of specific methods utilizing the present compositions include the following embodiments.

Rates of binding of movement of tRNA, and the variation of such rates in response to conditions of interest may be measured. Combinations of labeled materials suitable for such an application include labeling of a P-site tRNA and A-site tRNA with a FRET pair of fluorochromes, for example where one of the labeled tRNA is fMet-tRNA.

tRNA selection may be monitored by forming EF-Tu*GTP*aminoacyl-tRNA ternary complexes with the dye-labeled tRNAs, where binding to the A-site can be monitored by FRET with a dye-labeled tRNA in the P site. FRET between the elbow regions of the P-site and A-site tRNAs allows distinction between conformational states. The reaction mixture may further comprise competitive tRNAs, agents such as antibiotics that affect translation, variations in reaction conditions, e.g. salt concentrations, concentration of factors, temperature, etc.

Conformational events near the decoding site on the 30S or 40S subunit may utilize the previously described BIV peptide tagging strategy to label H44 of the 30S subunit. H44 forms extensive subunit interface contacts, as well as direct contacts with the codon-anticodon helix in the A-site. Fluorescence changes may be monitored in the decoding site upon tRNA binding to both the P and A site, either as a single molecule, or performing FRET measurements with labeled tRNAs Conformational events on the 50S subunit may be monitored using complexes labeled at protein L7/L12. This protein is a major portion of the factor binding surface, and is required for GTPase activation of EF-G and EF-Tu (see Hamman et al. (1996). J Biol Chem 271(13): 7568-73; Hamman et al. (1996) Biochemistry 35(51): 16680-6; Hamman et al. (1996) Biochemistry 35(51): 16672-9). The fluorescently-labeled ribosomes may be used to monitor EF-Tu binding by fluorescence changes or FRET. A double labeled L7 may be used to monitor change in FRET as ternary complexes are added to 70S particles. Where L7/L12 is singly labeled, a dye partner can be provided on the C70 of L10; and FRET between this dye pair used to monitor movement of the tetramer with respect to the body of the 50S subunit, upon addition of ternary complex.

Movements of rRNA domains in the 50S subunit can be determined by attachment of a fluorophore to a cross-linked puromycin substrate bound to the A loop of the peptidyl transferase center. Using FRET, measurements can be made between the labeled cross linker and either a labeled met-tRNAfMet in the P site or labeled L7/L12. These FRET pairs measure the relative position of the A loop-cross link to either the peptidyl transferase center or factor binding site. Changes in FRET may be measured as a function of addition of ternary complex, or tRNA anticodon stem-loop in the A site.

Intrasubunit conformational changes on the small subunit may be monitored through a double-labeled subunit. For example, one fluorescent label may be incorporated into the beak through the mutation of the beak loop to include a DNA hybridization sequence where a fluorescently-labeled DNA oligonucleotide is then hybridized to the loop. The second label, to the shoulder region, may be incorporated using the BIV tagging strategy, targeted to H16 or 17 of the shoulder region. FRET may be measured in an equilibrium binding assay upon addition of deacylated tRNA to the A-site, either cognate or non-cognate. Time-resolved FRET may be monitored upon addition of ternary complex to the surface-bound ribosomes. Intersubunit conformational changes may also be monitored using doubly-labeled ribosomal particles, for example by examining intersubunit bridge regions. Using the BIV peptide approach, mutations in H44 of the 30S subunit, and within domain IV of the 50S subunit, in particular H69 and H72 can create a dye-peptide binding site. Double labeling with Cy3/Cy5 partners will be achieved by labeling of isolated subunits, and reconstitution of 70S particles with the labeled subunits.

Using a rRNA tagging strategy, rRNA mutants can be readily studied in single-molecule functional assays. Detailed studies of severe phenotype mutations in rRNA are hindered by the inability to prepare pure populations of mutant ribosomes. By combining the rRNA mutation with the tagging mutation, only mutant ribosomes are observed in the single-molecule analysis. A limited number of mutations may introduced into rRNA, e.g. G530A, A1492/93G, etc., and the effects on rRNA conformational rearrangements during tRNA binding determined.

The time scales and nature of tRNA movements, EF-G binding, GTP hydrolysis and movement, and ribosomal conformational changes that occur during translocation are also monitored with the compositions of the present invention. Time scales of tRNA movement may be measured using 70S particles with labeled S21 protein, which bridges the two subunits in the region of the E site. A labeled tRNA is introduced, where the movement of the P-site tRNA into the E-site will give an increase in FRET as the labeled tRNA approaches labeled S21. Althernatively, the relative positions of tRNAs on the ribosome can be monitored by FRET between 2 dye labeled tRNAs. Translocation of the P-site tRNA can be initiated in several ways, to examine uncatalyzed and EF-G-catalyzed translocation, e.g. by the addition of puromycin, addition of competitive tRNA, addition of an elongation factor complex, combinations thereof, and the like. In these assays, the concentration of competitive unlabeled ligand can be varied to extract association rates, or analogs used to block specific steps.

Artificial mRNA encoding an alternating three amino acids can be used in a method of measuring rates of tRNA passage, where two or more of the component tRNA are labeled. Ternary complexes of the three tRNAs are formed, and added to surface-bound ribosomes complexed to the artificial mRNAs. The presence of either labeled tRNA on the ribosome is readily detected. When both labeled tRNAs are present in A and E sites, then FRET is observed. Alternating mRNA is also useful in screening for drug effects on translation.

The rates of EF-G conformational changes during translation can be monitored using fluorescently-labeled EF-G molecules. Single cysteine mutants of EF-G can be labeled (see Wilson and Noller (1998) Cell 92: 337-349), and changes in fluorescence of the different EF-G derivatives as GTP complexes monitored upon addition to 70S complexes with an empty A site, or to 70S ribosomes in an A/P hybrid state.

Labeled EF-G*GTP complexes may be used in conjunction with labeled ribosomal particles, for example to detect a FRET signal between H44 and domain IV, which is indicative of the movement of this EF-G domain into the decoding site, which is essential for tRNA movement. Labeled EF-G mutants may be used in conjunction with ribosomes containing labeled L7/L12, where a FRET signal between EF-G labeled in domain 11 and L7/L12 reveals initial binding of EF-G to the ribosome.

The binding of derivatized antibiotics to ribosomes may be monitored using single-molecule fluorescence, e.g. during analysis of translation to observe the residence time of the drug on the ribosome. The effects of antibiotics on ribosome conformation and basic steps of translation can be monitored using the methods described above by the addition of the drug to the reaction, and monitoring the effect on 30S subunit conformation, the 30S/50S subunit interface and L7/L12 conformation. FRET changes and kinetic parameters during decoding in the presence of antibiotic may be measured. The effects of antibiotics on EF-G binding, conformational changes, tRNA movement may be measured using the single molecule methods.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Experimental

To perform single-molecule spectroscopic analysis of a biomolecular system, the molecules are specifically localized on a derivatized quartz surface. The attachment to the surface allows spatial localization of the particle to the optical limit of the microscope without impairing its function

EXAMPLE 1

Ribosome Characterization

To characterize ribosomes using biophysical analysis, their chemical composition must be determined; ribosomes can be missing certain proteins (especially L7/L12) that decrease activity, or rRNA can be degraded. 70S ribosomal particles were purified from $E.\ coli$; subunits were dissociated and purified by sucrose density gradient centrifugation. The composition of the ribosomes was analyzed by gel electrophoresis. The RNA components (23S, 16S and 5S RNA) were all intact and present stoichiometrically. The protein composition was determined by two-dimensional electrophoresis; all 54 proteins were present. The presence of proteins most often present in sub-stoichiometric quantities, L7/L12 and S1, were monitored by native gel analysis of the ribosomal particles. The 30S subunit has different mobility plus or minus S1; likewise the 50S subunit has different mobility plus or minus L7/L12. It was shown that protein L7/L12 is present in stoichiometric amounts as a tetramer, whereas S1 is present in sub-stoichiometric ratios. Both proteins can be overproduced in the appropriate bacterial strains. The activity of the ribosome preps were checked using in vitro translation of gene 32 protein under standard conditions; the ribosomes showed appropriate activity in translation. These results demonstrate that ribosomes of defined composition can be prepared for further analysis.

EXAMPLE 2

Specific Surface Attachment of Ribosomes

Ribosomes can be specifically attached to quartz surfaces. Microscope slides were derivatized to provide a surface with streptavidin molecules on the surface. To detect ribosomal particles, 50S subunits were non-specifically labeled with Cy3 NHS esters, which react with surface-accessible amino groups. An average of 1 dye molecule per subunit was estimated using single-molecule fluorescence. A quaternary complex was then formed with 70S particles that have labeled 50S subunits, tRNAfMet, a short mRNA that corresponds to the first 3 codons of the gene 32 protein mRNA and a 18 nt DNA complementary to the 5' end of the mRNA. Two complexes were formed with the DNA either 3' biotinylated or not. The quarternary complexes were purified using a sucrose gradient and isolated. Ribosomal complexes at a concentration of 1 µM were flowed onto the quartz surface and then washed in buffer. Only ribosomal complexes with biotinylated DNA attach to the quartz surface. Cy3 fluorescence was monitored; localized spots showed that 50S subunits are localized. Since the ribosomal complexes are held to the surface by interaction between the P-site tRNA and mRNA, the presence of labeled 50S subunits means the entire complex has bound to the surface. The complexes are reversibly bound to the surface, as treatment with 50 mM EDTA releases the 50S subunits.

The 70S complexes were stably bound to the surface for minutes to hours. The dissociation rate of the complexes depends on solution conditions and ligand-bound state of the ribosome. A matrix of conditions was investigated to determine the stabilities of surface-bound ribosomal complexes. It was found that complexes are more stable at higher $Mg^{2+}$ concentrations and monovalent ion concentrations. This is consistent with the stabilization of RNA-RNA interactions at the subunit interface. The complex stability also increased at lower pH. Complex stability was also greatly increased by the presence of a P-site tRNA, and further increased by addition of an acyl-aminoacid on the tRNA.

Binding of transfer RNA within the surface-bound complexes was analyzed by co-localization of fluorescently-labeled tRNA with fluorescently-labeled ribosomes. Initiator tRNAfMet was methionylated by MetRS, and the free amino group of the Met-tRNAfMet was derivatized with Cy5 using NHS ester chemistry. Cy5-methionyl-tRNAfMet was purified by HPLC and complexes with Cy3-labeled 70S subunits (50S subunit labeled) mRNA and DNA were formed and purified by sucrose gradient centrifugation. These complexes were bound to the surface and Cy3 and Cy5 fluorescence was monitored. It was estimated that a lower limit of 35% of Cy3-labeled ribosomes have Cy5 tRNA bound; the low P-site occupancy may be increased by addition of increased tRNA concentration, but more likely results from hydrolysis of the aminoacyl-tRNA during complex formation. The advantage of single-molecule analysis can be seen here, as bulk measurements can not catalog ribosomes in this manner.

The surface-attached ribosomes are active in catalyzing peptide bond formation. The Cy5 tRNA complexes discussed above were used to test peptidyl transfer activity using the puromycin reaction. Puromycin is analog of aminoacyl tRNA, and binds to the A-site on the 50S subunit; it reacts to form a peptidyl-puromycin adduct that can no longer undergo chain elongation. With the complexes described above, puromycin reacts to form Cy5-met-puromycin, which is weakly bound by the ribosome and rapidly dissociates. Loss of Cy5 spots was examined as a function of time after addition of puromycin; Cy3 fluorescence was monitored simultaneously to assure that ribosomes do not dissociate during the time course of the experiment. Puromycin clearly causes release of Cy5 dye, and ribosomes are stable during the course of the experiment. The data are corrected for the rates of photobleaching of Cy5, which is insignificant on the time scale of the experiment, using shuttered excitation. All Cy5-tRNA reacts in this assay, and the rates of reaction correspond to previously measured rates for the puromycin reaction measured in bulk using biochemical methods.

The puromycin reaction on the surface is sensitive to solution conditions in a manner consistent with data from bulk measurements in solution. The rate of the peptidyl transferase reaction increases with increasing pH, as observed in bulk. This is consistent with a base-catalyzed reaction. The surface-based peptidyl transfer reaction is inhibited by antibiotics that inhibit peptidyl transfer. Chloramphenicol is a peptidyl transferase inhibitor that is a competitive inhibitor of the puromycin reaction. Addition of 1 mM chloramphenicol leads to the appropriate inhibition of the surface-based puromycin reaction. Acetylpuromycin, which has its reactive amino group blocked by acetylation, does not lead to Cy5 release.

Surface-bound ribosomes are competent for all steps of translation. Surface attached ribosomes can accept tRNAs delivered by elongation factor Tu with high efficiency. High intensity FRET is observed between dye-labeled tRNA in the P-site and the delivered tRNA in the A-site. Delivery of tRNA by Ef-Tu is blocked by antibiotics. FRET is greatly decreased in the presence of tetracycline, a translational inhibitor. Surface-bound ribosomes are also competent for translocation catalyzed by elongation factor G.

EXAMPLE 3

Labeling of Ribosomal Components and Ligands with Fluorescent Dyes

Labels were incorporated into (a) tRNAs, (b) ribosomal proteins, and (c) ribosomal RNA. For tRNA ligands, fluorescent dyes were incorporated on the amino acid of methionyl-tRNAfMet. tRNAs were also synthesized with a single amino linker that can be derivatized by NHS-ester chemistry. This has allowed body labeling tRNAs at critical functional sites, like the anticodon stem loop, the elbow region and 3' acceptor arm.

Ribosomal protein S21, which contains a single cysteine, was labeled. The S21 was labeled initially with maleamide tetramethylrhodamine; dye labeled protein was separated from unlabeled protein by HPLC. The labeled S21 was incubated with 30S subunits at high salt and 10-fold excess S21 to favor exchange of bound S21 for labeled S21. Complexes with tRNA and mRNA were assembled as described above using unlabeled 50S subunits. This lead to surface-bound complexes with single dye molecules attached to the ribosome. The intensity of observed rhodamine fluorescence is uniform for individual spots. Thus, ribosomal proteins can be labeled and incorporated into 70S particles.

A fluorescent label was incorporated in the heart of the A site of the 50S subunit. 5' 4sTCC-puromycin is an A-site substrate, which binds with higher affinity puromycin, due to additional ribosome contacts with C74 of tRNA. Upon radiation with light of 320 nm, 4sTCC-puromycin forms a cross link with G2553 in the A loop of 23S rRNA. This crosslinked puromycin is competent to perform the peptidyl transferase reaction. Cross-linking an oligonucleotide version of the cross-linking reagent, allows formation of a duplex with a 3'-Cy3 or Cy5 labeled oligonucleotide. Cross linking was performed, and complexes with unlabeled tRNA and non-specifically labeled 70S subunits were formed and purified by sucrose gradient centrifugation. Biochemical analysis localized the cross link to G2553, as predicted from prior studies. Single-molecule fluorescence analysis showed co-localization of the cross-linked fluorescent duplex with ribosomes; intensities were consistent with a single fluorophore per ribosome, and a cross linking efficiency of about 10%. These data show that rRNA dye labeling in active sites is possible.

Labeled S21, which binds in the E site, was used as a FRET partner for translocation of P-site tRNA towards the E-site. S21 was labeled at C21 as described above and tRNAfMet was labeled at the elbow in the D loop. S21 protein has been overexpressed and purified. An 15N-labeled sample was prepared; and a 1H-15N HSQC of the amide region determined. The dispersion of the spectrum was consistent with a weakly alpha helical structure, as supported by structure prediction and CD spectra.

Fluorescently-labeled DNA or RNA oligonucleotides were hybridized to ribosomes containing mutant rRNA. Labeled ribosomes bind specifically to derivatized surfaces. Ribosomes containing mutations in non-conserved regions of rRNA to allow fluorescent tagging were active in vivo and in vitro.

RNA oligonucleotides were synthesized using in vitro transcription with T7 RNA polymerase. To avoid RNA heterogeneity, ribozyme cleavage sites were engineered at the 3' and 5' end of the RNA. T7 polymerase for large-scale transcription was obtained in-house by an overexpression system. RNA was purified using preparative gel electrophoresis. RNA oligonucleotides with modified nucleotides, in particular 5-alkyl amino pyrimidines, were purchased from commercial sources and purified in-house.

EXAMPLE 4

Ribosome Preparation, Purification, and Labeling

E. coli MRE600 cells are grown to early log phase, and then rapidly cooled to 0° C. by pouring over ice, to preserve polysomes. Cells are pelleted and lysed by lysozyme/freeze thaw-fracture method. Cell debris is removed by initial slow spin, and then ribosomes are pelleted from the supernatant by 100 Kxg spin. To improve selection of active ribosomes, polysomes are separated from ribosomes and subunits by gel filtration; the isolated polysomal ribosomes are dialyzed against low Mg2+ buffer to dissociate polysomes and 70S particles to subunits. Isolated subunits are purified by sucrose density gradient centrifugation; Subunits can be stored at −80° C.

Gel electrophoretic analysis of ribosomal proteins and particles. Native gels are run using a modification of published procedures (Dahlberg et al. (1969) J Mol Biol 41(1): 13947). 2.75% polyacrylamide/0.5% agarose is the standard gel matrix. The gel buffer and running buffers are 25 mM Tris-acetate, 6 mM KCl, 2 mM MgCl, 1 mM DTT. 1% w/v sucrose is added to the gel matrix. Gels are run in the cold room with buffer recirculation and continuous cooling at 1° C. Two dimensional gel electrophoresis of ribosomal proteins is performed with a the Bio-Rad protean 11 xi 2d electrophoresis system using published protocols (Agafonov et al. (1999) PNAS 96(22): 12345-9).

Mutant Ribosomes. Mutations are incorporated into either low or high copy plasmids for expression of ribosomes with mutant subunits, using standard protocols, Recht et al. (1999) J. Mol. Biol. 262: 421-436. Mutations with non-lethal phenotypes can be expressed from high copy plasmids, and can be expressed as a pure population using an E. coli strain in which all 7 copies of the rRNA operon has been deleted (Asai et al. (1999) PNAS 96(5): 1971-6). Mutations that confer lethal phenotypes must be expressed using a repressed plasmid system; expression of the mutant ribosomal RNA upon induction can lead to mutant ribosomes as 20-40% of the total population of ribosomes.

Protein expression and purification. Protein expression strains are available for the following proteins: EF-Tu, EF-G, cysteine (−) mutant, his-tagged; EF-G, cysteine (−) mutant, C301 mutation, his-tagged; EF-G, cysteine (−) mutant, C506 mutation, his-tagged; EF-G, cysteine (−) mutant, C585 mutation, his-tagged; S1, S21, IF1, IF3, RRF, L7/L10 (co-expressed), L7/L10 (co-expressed): L7 C37, L7/L10 (co-expressed): L7 C63, L7/L10 (co-expressed); L7 C58, L10, L10 deletion mutant that binds only one dimer of L7; Methionyl tRNA synthase, Transformylase. Proteins are overexpressed in E. coli. Purification follows standard methods. For His-tagged proteins, a single Ni column is sufficient. For untagged proteins, multicolumn purification using FPLC is performed.

tRNA aminoacylation. Deacylated tRNAs fMet, Phe and Lys can be purchased, for example from Sigma. tRNAfMet is aminoacylated using purified MetRS; Aminoacylation is performed on large scale using 20 µM tRNA in standard aminoacylation buffers. Aminoacylated tRNA is purified from non-acylated tRNA using HPLC. Other tRNAs are aminoacylated using a mixture of E. coli aminoacyl-tRNA synthetases Dye Coupling. Cy3 (Max 550 nm, emission max 570 nm) and Cy5 (Max 649 nm, emission max 670 nm) are purchased as either N-hydroxy-succinimyl (NHS) esters or maleimides with 6 carbon linkers (Amersham-Pharmacia); amino groups are derivatized using NHS ester chemistry, whereas —SH groups are derivatized with maleimide chemistry. For dye labeling of the NH2 group of methionyl-tRNAfMet, the reaction is performed in 100 mM triethanolamine hydrochloride in 80% v/v DMSO the final pH of the solution is 7.8. tRNA is soluble in this solution up to 100 µM and dyes are added to this solution up to 4 mM final concentration. The reaction takes place at 37° C. for 8-10 hrs and is quenched by ethanol precipitation. Free dyes are removed from tRNA by spin-column gel filtration and the desired product is easily isolated in pure because the dye molecule retards migration by more than 40 minutes from the unlabeled tRNA by HPLC. As an example of cysteine labeling, S21 is efficiently labeled with maleimide containing compounds in 7 M Guanidinium Chloride/10 mM K-Hepes pH 6.5/2 mM TCEP (a non-sulfur based reducing agent) by incubation 4° C. overnight in the presence of a 50× molar excess of labeling reagent (Cy3/5-maleimide from Amersham-Pharmacia). Before modification, the cysteine is reduced in 20 mM DTT 37° C. and gel filtered into incubation buffer Free dye is separated from S21 using cation exchange resin. Coupling efficiency is monitored by gel electrophoresis.

Ligation of RNAs. RNAs are ligated on large scale using T4 RNA ligase; we have achieved ligation efficiencies on large scale of 10-50%. To avoid self ligation, the 3' strand contains both 5' and 3' phosphate. The 3' phosphate is generated by transcription and hammerhead ribozyme cleavage at the 3' end. The 5' strand has a 3' OH (a 5' OH is preferable also to avoid self ligation. Ligation reactions are performed in standard ligase buffer at RNA concentrations of 50-100 µM; RNA strand concentrations, Mg2+ concentration and polyethylene glycol concentrations are optimized on small-scale reaction for each sequence. We have used these ligation methods on large RNAs rich in secondary structure, such as tRNA and the HCV IRES. Three-way ligations will be performed in a stepwise manner.

Single-molecule Fluorescence Spectroscopy. Single molecule fluorescence spectroscopy is a powerful means of monitoring conformational dynamics of complex biological systems. Single molecule analysis can detect rare conformational events that are not observed in bulk, ensemble-averaged measurements. It allows heterogeneity in the system to be sorted and characterized; this is particularly important in complex, multifactor processes such as translation. For multistep processes such as translation, single molecule analysis eliminates the requirement for synchronization of large numbers of molecules. The time resolution of the single molecule fluorescence instrumentation (from 1-100 ms) is ideal to deal with the relatively slow processes of translation. The distance scales probed by fluorescence resonance energy transfer (FRET) (20-80A) are appropriate for the large size (250A) of the ribosomal particle.

The internal reflectance (TIR) microscope allows simultaneous detection of hundreds of single molecules, with a time resolution of 100 ms. The fluorescent samples are excited by the evanescent wave generated by total internal reflection of dual laser excitation (532 nm and 635 nm). Fluorescence is detected using a CCD camera, after the radiation has passed through a dichroic (635 nm longpass) filter; cy3 and cy5 emission is measured on two halves of the CCD. In the scanning confocal microscope, fluorescence is dual excited at 532 and 635 nm and detected using avalance photodiodes. In this instrument, the fluorescence of a single molecule (as opposed to a field of molecules, as in the TIR microscope), is monitored with a time resolution of 1 ms. This instrument is used for rapid kinetic measurements, as most critical conformational steps in translation occur more slowly than 1 ms. For both instruments, laser powers are 0.3-0.5W. The instruments are controlled, and data are processed using in-house software.

What is claimed is:

1. A translationally competent isolated bacterial ribosome complex bound to a solid surface at a specific attachment site on an RNA of said ribosome complex wherein said RNA is a rRNA; wherein said specific attachment site comprises one member of a specific binding pair bound to said solid surface, and a polynucleotide linker which is (a) attached to said solid surface through a complementary binding pair member which is covalently attached to said linker and (b) hybridized to a surface accessible hairpin loop present on said rRNA.

2. The ribosome complex of claim 1, wherein said surface hairpin loop is naturally occurring.

3. The ribosome complex of claim 2, wherein said naturally occurring surface accessible hairpin loop is expanded by from about 8-18 nucleotides.

4. The ribosome complex according to claim 1, wherein said surface accessible hairpin loop is selected from the group consisting of the 16S rRNA loop H6, 16S rRNA loop H10, 16S rRNA loop H26, 16S rRNA loop H33a, 16S rRNA loop H39, 6S rRNA loop H44, 23SrRNA loop H9, 23SrRNA loop H68 and 23SrRNA loop H101.

5. A solid surface comprising an array of translationally competent ribosome complexes according to claim 1.

6. The array of claim 5, wherein said solid surface is quartz.

7. The ribosome complex of claim 1, wherein said ribosome complex further comprises a fluorescent label.

8. The ribosome complex of claim 7, wherein said ribosome complex comprises two distinct fluorescent labels, wherein said labels are a donor/acceptor pair.

9. The ribosome complex of claim 7, wherein the fluorescent label is present on one or more of: tRNA, rRNA, mRNA, and ribosomal protein.

10. The ribosome complex of claim 9, wherein said tRNA is directly labeled.

11. The ribosome complex of claim 9, wherein said ribosomal protein is directly labeled.

12. The ribosome complex of claim 11, wherein said ribosomal protein is S21 or S5.

13. The ribosome complex of claim 9, wherein said rRNA is genetically modified to comprise a peptide binding site, and wherein a fluorescently labeled peptide is bound to said modified rRNA.

14. The ribosome complex of claim 13, wherein said fluorescently labeled peptide is BIV Tat.

15. The ribosome complex of claim 13, wherein said fluorescently labeled peptide is HIV-Rev.

* * * * *

UNITED STATES PATENT AND TRADEMARK OFFICE
CERTIFICATE OF CORRECTION

| | | |
|---|---|---|
| PATENT NO. | : 7,297,532 B2 | Page 1 of 1 |
| APPLICATION NO. | : 10/352504 | |
| DATED | : November 20, 2007 | |
| INVENTOR(S) | : Joseph D. Puglisi et al. | |

It is certified that error appears in the above-identified patent and that said Letters Patent is hereby corrected as shown below:

In the Specification

Please replace the Statement Regarding Government Rights beginning on column 1, line 6, with the following revised statement:

STATEMENT REGARDING GOVERNMENT RIGHTS

This invention was made with Government support under contract GM051266 awarded by the National Institutes of Health. The Government has certain rights in the invention.

Signed and Sealed this
Eighth Day of September, 2015

Michelle K. Lee
*Director of the United States Patent and Trademark Office*